(12) United States Patent
Webber et al.

(10) Patent No.: US 6,255,058 B1
(45) Date of Patent: Jul. 3, 2001

(54) IMMORTALIZED AND MALIGNANT HUMAN PROSTATIC CELL LINES

(75) Inventors: Mukta M. Webber, Eagle, MI (US); Johng S. Rhim, Potomac, MD (US)

(73) Assignees: Board of Trustees operating Michigan State University, East Lansing, MI (US); The United States of America as represented by the Department of Health and Human Services, Washington, DC (US)

(*) Notice: Subject to any disclaimer, the term of this patent is extended or adjusted under 35 U.S.C. 154(b) by 0 days.

(21) Appl. No.: 09/172,475

(22) Filed: Oct. 14, 1998

Related U.S. Application Data (62) Division of application No. 08/234,843, filed on Apr. 28, 1994, now Pat. No. 5,824,488.

(51) Int. Cl.[7] .................. G01N 33/574; G01N 33/53; C12N 5/00; C12N 5/02; C12N 5/08
(52) U.S. Cl. ................ 435/7.23; 435/7.1; 435/325; 435/366; 435/371; 435/377; 436/64
(58) Field of Search ................. 435/7.21, 7.23, 435/325, 366, 371, 377; 436/64

(56) References Cited

PUBLICATIONS

Journal of Cellular Biochemistry, Supplement 16H: 1–8 (1992).
Tilley, W.D., Cancer Research 50, 5382–5386 (1990).
Webber, M. M., et al., Carcinogenesis, vol. 17 No. 8 pp. 1641–1646 (1996).
Webber, M. M. et al., Radiation Oncology Investigations 3:358–362 (1996).
Wishart, G.C., et al., Br. J. Cancer, 62(5): 758–761 (1990).
Weisenthal, Larry M., et al., Cancer Research 43: 749–757 (Feb. 1983).
Webber, M. M. and A. Waghray, Clinical Cancer Research vol. 1: 755–761 (1995).
Wang, Y., et al., Clin. Exp. Metastasis 13:196–202 (1995).
Waghray, A., and M. M. Webber, Clinical Cancer Research. vol. 1: 747–753 (Jul. 1995).
Tishler, R.B., et al., Cancer Research 52: 3495–3497 (Jun. 15, 1992).
Steele, C., et al., Cancer Research 53:2330–2337 (May 15, 1993).
Slawin, K., et al., Cancer Research 53:4461–4465 (Oct. 1, 1993).
Siegsmund, M. J., et al., The Journal of Urology, vol. 151:485–491 (Feb. 1994).
Shalinsky, D. R., et al., Clinical Cancer Research vol. 2, 511–520 (Mar. 1996).
Ripoll, Emilia A. Perez, et al., The Journal of Urology vol. 136, (1986).
Pollard, M., et al., Cancer Research, 51:3610–3611 (Jul. 1, 1991).

(List continued on next page.)

Primary Examiner—Anthony C. Caputa
Assistant Examiner—Jennifer Hunt
(74) Attorney, Agent, or Firm—Ian C. McLeod (57) ABSTRACT

Immortalized malignant human prostatic epithelial and fibroblast cell lines containing DNA of a human papillomavirus (HPV) and similar cell lines containing DNA of a human papillomavirus and an activated viral ras oncogene, such as v-Ki-ras. The cell lines are useful for research on drugs for treatment of prostatic cancer and other diseases. The cell lines are useful for research on causes, treatment and prevention of prostate cancer, benign prostatic hyperplasia, male infertility, birth defects, aging and assessment of environmental toxic agents.

3 Claims, 5 Drawing Sheets

PUBLICATIONS

Hiscox, S., et al., Clin. Exp. Metastasis 13:396–404 (1995).
Hei, T. K., et al., Cancer Research 53:1368–1372 (1993).
Bergman, A. M., et al., Clinical Cancer Research vol. 2:521–530 (Mar. 1996).
Cussenot, O., et al., Journal of Urology 143, 881–886 (1991).
Kaighn, M. E., et al., Cancer Research, 49, 3050–3056 (1989).
Kaur, P., et al., Journal of Virology 62, 1917 (1988).
Woodworth, C. D., et al., Cancer Research 48, 4620 (1988).
Viola et al., N. England J. Med. 314:133 (1986).
Carter, B. S., et al., Cancer Research 50, 6830 (1990).
McNicol, J. P., et al., Journal of Urology 145, 850 (1991).
Anwar, K., et al., Cancer Research 52, 5991 (1992).
Webber, M. M., et al., V: pp. 3–24 (1988).
Konishi, N., et al., Cancer 69, 2293 (1992).
Rhim, J. S., et al Oncogene 4, 1403 (1989).
Rhim, J. S., et al., Science 227, 1250 (1985).
Tanaka, K., et al., Cell 35, 457 (1983).
Maloy, W. L., et al., Proceedings of the National Academy of Science USA 81, 1216 (1984).
Rhim, J. S., et al., Science 232, 385 (1986).
Lee et al., Internat. J. Oncol. 4:821 (1994).
Patterson, Methods Enzymol. 58:141 (1979).
MacDonald et al., Exp. Cell. Res. 50:471 (1968).
Thompson, Methods Enzymol., 48:308 (1979).
Hsu et àl Proc. Natl. Acad. Sci. USA 75:2003 (1978).
Latt et al. In: S. Wolffe (ed.), Sister Chromatic Exchanges, New York: Plenum Press pp. 17–40 (1982).
Stanbridge et al., Science 215:252–259 (1982).
Davis et al., Methods in Molecular Biology, New York: Elsevier (1986).
Proceedings of the American Association for Cancer Research 34:117 (Mar. 1993).
Grynkiewicz et al, J. Biol. Chem. 260:3440–3450 (1985).

IMMORTALIZED AND MALIGNANT HUMAN PROSTATIC CELL LINES

This application is a divisional of application(s) application Ser. No. 08/234,843 filed on Apr. 28, 1994 now U.S. Pat. No. 5,824,488.

BACKGROUND OF THE INVENTION (1) Field of the Invention

The present invention relates to human prostatic epithelial and fibroblast cell lines which have been immortalized. In particular, the present invention relates to non-malignant cell lines immortalized with DNA of human papillomavirus (HPV) and malignant cell lines containing DNA of HPV and ras oncogene.

(2) Description of Related Art

Human cells are generally difficult to grow and maintain in long-term cultures in vitro. They have a limited life span in culture, grow for a short time and usually after 4 or 5 sub-cultures, they undergo senescence and die.

Prostate cancer is the leading cancer in men in the United States, in terms of incidence. Thirty-two percent (32%) of all cancers in men arise in the prostate. It is estimated by the American Cancer Society that 200,000 new cases of prostate cancer will occur in the U.S. in 1994. Prostate cancer is the second leading cause of death from cancer and 38,000 deaths are estimated to occur in 1994. African American men have the highest incidence of prostate cancer in the world, which is almost twice as high as that in white men and more than 600 times higher than in men from Thailand. One in 10 men in the U.S. by age 85 will develop prostate cancer in his lifetime. An estimated 11 million men have latent or clinical prostatic carcinoma. Approximately sixty-five (65%) of the cases already have metastatic disease at the time of diagnosis. The survival rate is less than 20% after metastasis.

The causes of prostate cancer are not known at the present time. A study of the causes, prevention and treatment has been hampered by the fact that no good animal or cell models are available. Although rat prostatic cells have been used extensively for such studies, rat prostate is not homologous to the human prostate, thus, it is not an ideal system to use.

There is a need for cell lines derived from normal human prostate which can be used for studies on the process of prostate cancer development in man and to identify agents which may cause or prevent prostate cancer.

Attempts have been made to immortalize human adult prostatic epithelial cells using a monkey virus (Simian virus SV40; Cussenot, O., et al., Journal of Urology 143, 881–886 (1991); Kaighn, M. E., et al, Cancer Research, 49, 3050–3056 (1989); Lee et al., Internat. J. Oncol. 4:821–830 (1994)). Only a monkey virus (SV40) fetal and adult human prostatic epithelial cells have been immortalized.

Human papillomavirus-18 (HPV-18) has been shown to immortalize human epithelial cells such as keratinocytes and cervical cells (Kaur, P., et al., Journal of Virology 62, 1917–1924 (1988); and Woodworth, C. D., et al., Cancer Research 48, 4620–4628 (1988)). The human papillomaviruses had never been used with human prostatic cells. An abstract was published in March 1993 describing an HPV immortalized prostatic epithelial cell line by the inventors and others; however, there was no disclosed method for producing the cells, particularly the use of a virus carrying a v-ki-ras oncogene for this purpose (Proceedings of the American Association for Cancer Research 34:117 (March 1993)).

There is increasing evidence for the involvement of the ras oncogenes and HPV infection in human prostatic carcinogenesis. Expression of activated ras oncogene has been demonstrated in human prostate adenocarcinomas (Viola et al., N. England J. Med. 314:133–137 (1986)). Additionally, a relatively high frequency (27%) of Ki-ras codon 12 mutation in human prostate carcinomas has also been detected by PCR amplification (Carter, B. S., et al., Cancer Research 50, 6830–6832 (1990)). In separate studies, a high prevalence of high-risk HPV DNA in human prostate carcinomas has been described (McNicol, J. P., et al., Journal of Urology 145, 850–853 (1991)). PCR analysis of type-specific HPV-sequences has been used to assess the prevalence of HPV DNA in prostate tissues from 83 Canadian patients. HPV DNA was found in 35 of 56 benign prostatic hyperplasia and in 14 of 27 prostate carcinomas. At least in one study, development of disease correlated with both the presence of HPV sequences and the activation of cellular ras genes (Anwar, K., et al., Cancer Research 52, 5991–5996 (1992)). Anwar et al. examined the frequency of ras mutations and the presence of high-risk HPV DNA sequences in 75 specimens from Japanese patients with prostate carcinomas using PCR amplification (Anwar, K., et al., Cancer Research 52, 5991–5996 (1992)). Mutant ras genes were present in 41% of cases and the frequency of ras mutations and HPV infection increased in patients with advanced tumors.

OBJECTS

It is therefore an object of the present invention to provide an immortalized non-malignant human prostatic epithelial cell line. Further, it is an object of the present invention to provide a malignant human epithelial cell line derived from the immortalized, non-malignant cell line. Further still, it is an object of the present invention to provide cell lines which are useful for research on prostatic cancer in vitro and for other purposes as set forth in detail hereinafter. A further objective of the present invention is a method for conversion of a non-tumorigenic, immortalized cell into a tumorigenic cell using a virus containing an oncogene, by exposure to radiation or by exposure to a chemical carcinogen. It is also an object of the present invention to provide methods and kits for screening carcinogenic agents or potential chemotherapeutic, anti-invasive, anti-metastatic and chemo-preventive agents using an immortalized non-malignant and/or malignant adult human prostate epithelial cell line.

These and other objects will become increasingly apparent by reference to the following description and the drawings.

DESCRIPTION OF THE DRAWINGS

FIG. 4 is a Western immunoblot showing expression of p21 ras protein in Ki-MuSV transformants. Subconfluent cultures of a Ki-MuSV transformed human keratinocyte line (lane 1), HPV-18 transfected HPE clone C-1 line (lane 2), Ki-MuSV infected HPV-18 HPE clone C-1 line (lane 3) and tumor line 129 Nu 3120-3 (lane 4) were rinsed with phosphate-buffered saline and lysed with a buffer containing 50 mM Tris-HCl, pH 7.5, 150 mM NaCl, 0.1% SDS, 1.0% Triton X-100, and 1.0, Na deoxycholate. The protein concentration of the lysates was determined and equivalent amounts of protein from each cell line were immunoprecipitated with either a pan-reactive mouse antibody against p21. The resulting immunoprecipitates were fractionated on a 12.5% polyacrylamide-SDS gel. After electrophoresis, proteins on the gel were electrotransferred onto a nitrocellulose membrane which was then reacted against the same antibody against p21. The immunocomplex on the nitrocellulose membrane was visualized by a subsequent reaction with $^{125}$I-labeled protein A. Positions of the endogenous wildtype p21 doublet (arrowhead) and the exogenous activated p21 doublet (arrow) are indicated. The molecular weight ($M_r$) markers used were 97.4, 69, 46, 30 and 14.3 kilodaltons.

DESCRIPTION OF PREFERRED EMBODIMENTS

The present invention relates to an immortalized non-malignant or malignant human prostatic epithelial or fibroblast cell line free of other cell lines and containing DNA of a human papillomavirus.

The primary prostatic cells to be immortalized can be from various donors and cell sources. The cells can be epithelial cells and fibroblasts. The epithelial cells include stem, basal, intermediate and differentiated luminal cells.

Alternatively, the non-malignant immortalized cells of the present invention can be made malignant by exposure to a virus, to radiation or to chemical carcinogens including for example N-methyl-N'-nitro-N-nitrosoguanidine (MNNG) or N-methyl-N-nitrosourea (NMU) and by promotion with tumor promoters such as 12-O-tetradecanoylephorbol-13-acetate (TPA). All of this is well known to those skilled in the art.

Further the present invention relates to a method for producing an immortalized malignant human prostatic epithelial or fibroblast cell line which comprises: providing non-malignant human prostatic epithelial or fibroblast cells with DNA of a human papillomavirus virus; and transforming the human prostatic epithelial or fibroblast cells with DNA of a virus which causes the non-malignant cell line to become malignant to thereby produce the-malignant cell line.

Further still, the present invention relates to a method for producing an immortalized human prostatic epithelial or fibroblast cell line which comprises: providing non-malignant human prostatic epithelial cells in a culture; and transfecting the epithelial cells in the culture with DNA of a human papillomavirus so that the cell line is immortalized. This cell line is used to produce the malignant cell line.

Human prostatic epithelial or fibroblast cells are immortalized using the entire Human Papillomavirus (HPV) genome or portions thereof. The HPV DNA may be obtained from different strains of HPV which are associated with cancer especially cancer of the breast, cervix, prostate or urogenital tract. The HPV DNA may be obtained from different strains of HPV which are isolated from malignant or benign tumors taken from the breast, cervix, prostate or urogenital tract of humans. Examples of such strains of HPV include but are not limited to HPV-18, HPV-31, HPV-33 and the like.

In one embodiment the cells are immortalized using the entire HPV genome from HPV-18, or HPV-31 and the like. In another embodiment, the human prostatic epithelial or fibroblast cells are immortalized using at least the E7 DNA portion of the genome or at least the E6 DNA portion of the genome or combinations thereof. In one embodiment a DNA sequence homologous or significantly homologous to the DNA sequence of E6 or E7 of HPV is used to immortalize human prostatic epithelial or fibroblast cells. In another embodiment, the cells are immortalized using at least the E7 DNA portion in combination with the E6 DNA portion of the HPV-18 genome.

Further, the present invention relates to a kit for screening a carcinogenic or chemotherapeutic agent comprising an immortalized human prostate epithelial or fibroblast cell line or derivative thereof containing DNA of a human papillomavirus. Particularly included are other ras oncogenes such as Ki-ras oncogene.

The present invention relates to a method for testing carcinogenicity of an agent comprising culturing the previously described non-malignant cell line previously described with an agent suspected of being carcinogenic and determining formation of an abnormal cellular mass by said cell line, the formation of the abnormal cellular mass being indicative of carcinogenicity of said agent.

The present invention also relates to a method for testing anti-invasive activity of an agent comprising culturing the malignant cell line previously described with a potential anti-invasive agent and determining invasive ability of said cell line being indicative of an anti-invasive activity of said agent.

The present invention also relates to a method for testing anti-metastatic activity of an agent comprising growing the malignant cell line previously described in nude mice, with a potential anti-metastatic agent and determining the metastatic ability of the tumor generated from the said cell line being indicative of an anti-metastatic activity of said agent.

The present invention also relates to a method for testing anti-angiogenic activity of an agent comprising growing the cell line previously described in vitro, in nude mice and in chick chorioallantoic membrane with a potential anti-angiogenic agent and determining angiogenic ability of said cell line being indicative of an anti-angiogenic activity of said agent.

The preferred cell lines are deposited with the American Type Culture Collection in Manassas, Va. The immortalized cell line with HPV-18 is deposited as ATCC CRL-11609 (RWPE-1). The immortalized, and Ki-ras transformed malignant cell line is deposited as ATCC CRL-11610 (RWPE-2). The deposits are under the Budapest Treaty.

V-Ki-ras from Ki-MuSV (Kirsten murine sarcoma virus) is a mutated ras viral oncogene (v-ras) with the ability to induce a malignant transformation of the cell line. The C-ras are normal proto-oncogenes which are expressed transiently in normal prostatic epithelial cells. In the preferred form, the Ki-MuSV is used as a hybrid with baboon endogenous virus (BaEV).

This invention demonstrates the first malignant transformation of adult human prostatic epithelial cells in culture by a combination of viral oncogenes. The invention particularly demonstrates the sequential involvement of HPV-18 and activated Ki-ras in the malignant conversion of human prostate epithelial cells and in particularly offers also a unique in vitro model system for further analysis of molecular events underlying prostate carcinogenesis.

In order to obtain further insights into the mechanism of prostatic carcinogenesis, newly-developed tissue culture methods were used to ascertain whether HPV-18 or Kirsten murine sarcoma virus (Ki-MuSV) containing an activated Ki-ras oncogene could confer a malignant phenotype on early passage human prostate epithelial cells. The present invention shows the immortalization of normal human prostatic epithelial cells by polybrene (Hexadimethrine bromide from Aldrich Chemical Co., Product No. 10768-9, Milwaukee, Wis.) induced DNA transfection of the HPV-18 genome and subsequent conversion of such non-tumorigenic but immortalized cells into tumorigenic cells by the introduction of an activated Ki-ras oncogene.

The present invention provides direct evidence for the sequential involvement of HPV-18 and Ki-ras in the malignant conversion of human prostatic epithelial cells and offers a unique in vitro model system for further analysis of molecular events underlying prostate carcinogenesis.

EXAMPLE 1

Epithelial cells were derived from the histologically normal prostate of a 54 year old white male undergoing a cystectomy for bladder carcinoma. The tissue was minced and digested in RPMI-1640 medium (GIBCO 11875-051, Grand Island, N.Y.) containing 5% fetal bovine serum and 400 u/ml collagenase (Webber, M. M., In Vitro Models for Cancer Research. In M. M. Webber, L. I. Sekeley, Eds., Vol. V. pp.3–24 (1988)). The isolated prostatic epithelial acini were plated into fibronectin and type IV collagen coated plates in keratinocyte serum-free medium containing 25 mg bovine pituitary extract and 2.5 $\mu$g EGF/500 ml K-SFM (GIBCO k-SFM, 10005-018, Grand Island, N.Y.). Secondary cultures grown in keratinocyte serum-free medium were used for immortalization.

Figure 2:
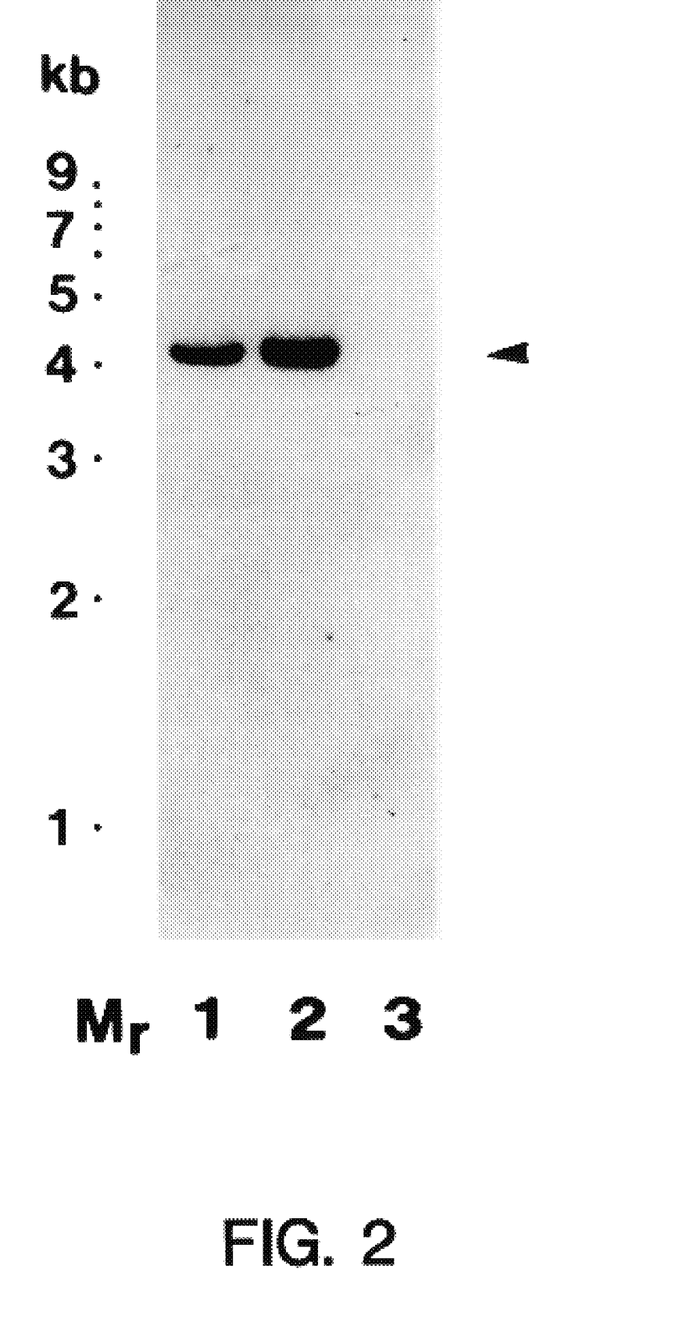
FIG. 2 shows a Southern blot showing a hybridization analysis of BamHI-digested genomic DNA from HPV-18 transfected human prostate epithelial (HPE) cell clones using a 1.5-xb XbaI DNA probe that spans the 3' end of E6, the entire E7, and the 5' end of E1 coding regions of HPV-18 as shown in FIG. 2A. The arrowhead shows an approximately 4.2-kb fragment that is indicative of the presence of the HPV genome in the appropriate clones. The locations of the molecular weight markers ($M_r$) used are shown on the left. Lane 1: HPV-18 transfected HPE clone A-2. Lane 2: HPV-18 transfected HPE clone C-I. Lane 3: Early passage HPE cells (negative control).
Figure 2A:
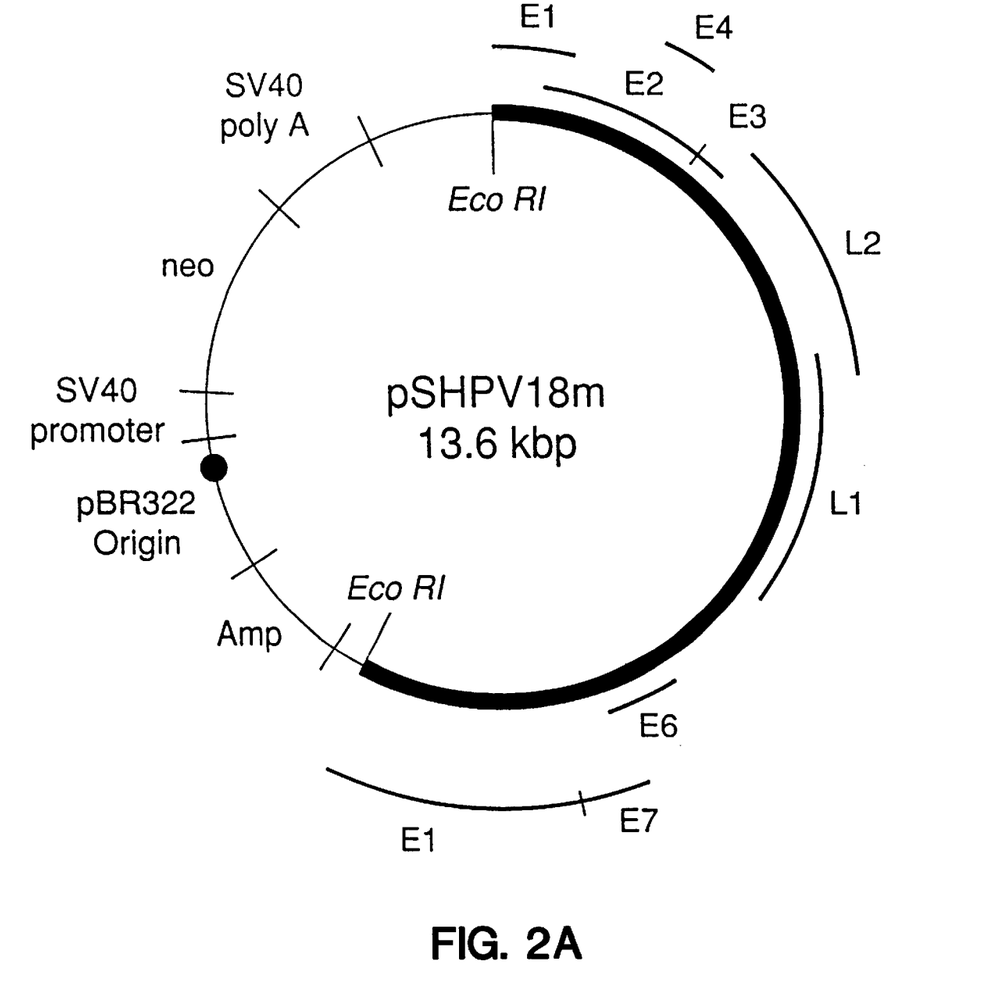
FIG. 2A is a plasmid diagram of plasmid pSHPV-18m which contains a single copy of the HPV genome inserted into the Eco R1 site of pSV2neo.

Source of HPV type 18 DNA: Plasmid pSHPV-18m contains a single copy of the HPV 18 genome inserted into the Eco RI site of pSV2 neo as described by Woodworth et al, Cancer Res 48:4620–4628 (1988). A genomic map of pSHPV-18m is shown in FIG. 2A.

Transfection: Polybrene-induced DNA transfection was carried out as described in Rhim et al., Oncogene 4:1403–1409 (1989). Cells were transfected with 10 $\mu$g of DNA using polybrene at a concentration of 10 $\mu$g/ml and incubated at 37° C. overnight. The cells were then shocked with 30% DMSO for 4 minutes. Five days after transfection the cells were subcultured at a 1:2 ratio approximately weekly. The cell culture medium was changed twice weekly.

TABLE 1

| Cells | Passages in culture (number) | Activated Ki-ras expression | Nude mice with tumors/mice inoculated* |
|---|---|---|---|
| Parental cells | <5 | ND | ND |
| plus Ki-MuSV | <5 | ND | ND |
| plus HPV-18 | >30 | – | 0/5 |
| plus HPV-18 + Ki-MuSV | >30 | + | 4/5** |

*Nude mice were inoculated with 10⁷ cells.
**tumors were reestablished in tissue culture and confirmed to resemble the cells of origin by karyological analysis.
ND = not done.
Table 1 shows the biological properties of adult human prostatic epithelial cells exposed to Ki-MuSV and/or HPV-18 DNA.

EXAMPLE 2

A number of cell lines were isolated from individual colonies using cloning cylinders and stored frozen in liquid nitrogen. Two clones with selected, designated A-2 and C-1, for further characterization. Both A-2 and C-1 cells had the typical polygonal arrangement of epithelial cells (FIG. 1A) but were less polygonal than the parental cells. Both cell lines have apparently an unlimited life-span; each has been successfully subcultured for more than 30 passages over the course of 1 year with no evidence of decreased proliferative capacity as shown in Table 1.

Figure 1A:
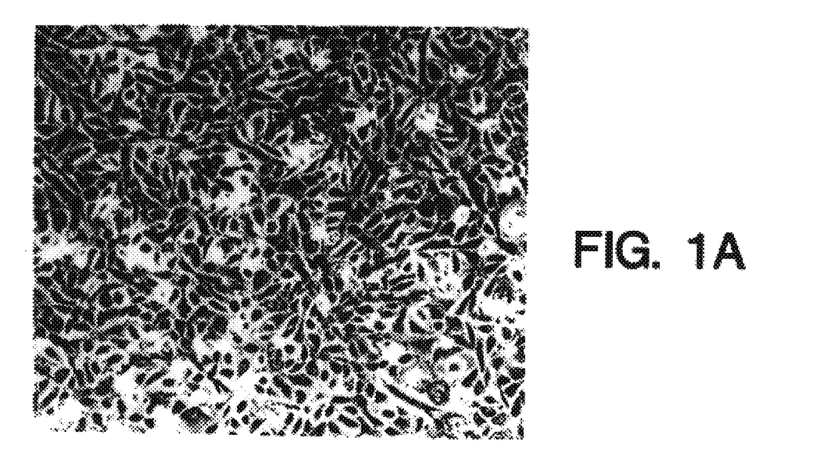
FIGS. 1A and 1B are photomicrographs showing a comparison of the morphology of HPV-18 DNA transfected adult human prostatic epithelial clonal line C-1 (FIG. 1A) with Ki-MuSV-transformed HPV-18 DNA transfected C-1 clonal line (FIG. 1B).
Figure 1B:
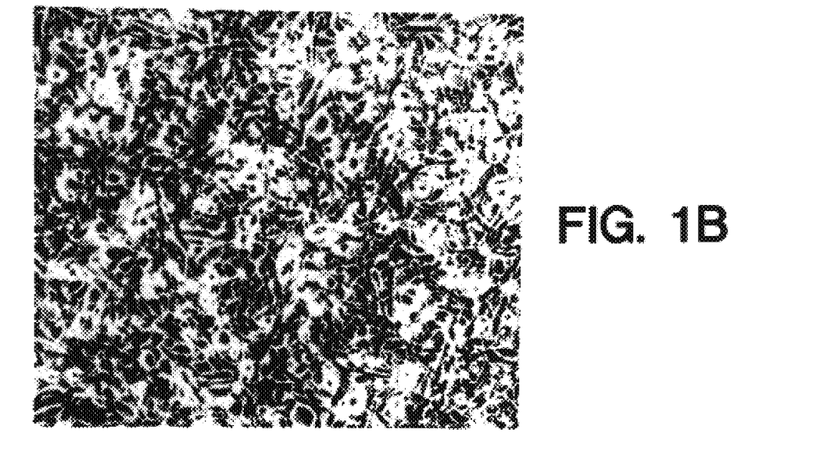
Figure 1C:
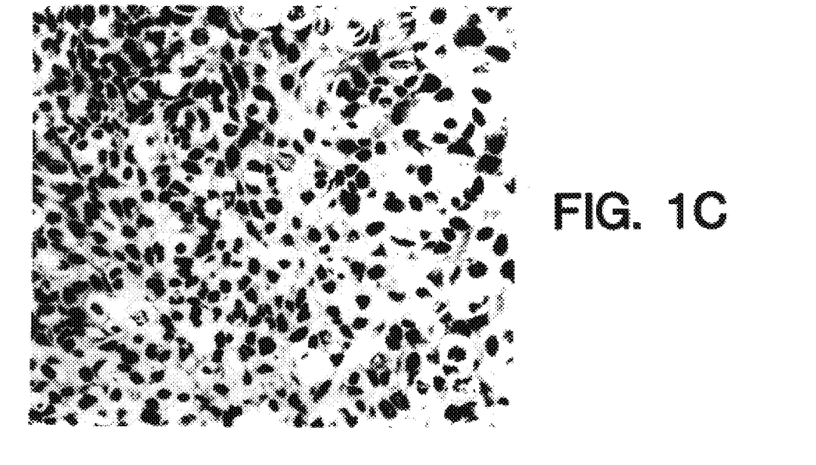
FIG. 1C is a photomicrograph showing hematoxylin-and-eosin stained section of a poorly-differentiated carcinoma produced by inoculation of the Ki-MuSV-transformed HPV-18 DNA transfected C-1 clonal line into adult 129J nude mice (×120).

To confirm that the two clones do contain the transfected HPV-18 DNA, Southern blot hybridization analysis (Tanaka, K., et al., Cell 35:457–465 (1983)) was carried out using genomic DNA that had been digested with BamHI and a 1.5-kb XbaI DNA probe that spans the 3' end of E6, the entire E7, and the 5'end of E1 coding regions as shown in FIG. 2A. The detection of an approximately 4.2-kb fragment in both clones A-2 and C-1, but not in the early passage parental cells demonstrates that HPV-18 sequences have been integrated into both cell clones as shown in FIG. 2. FIGS. 1A to 1C show the morphology of the cell lines.

Figure 3A:
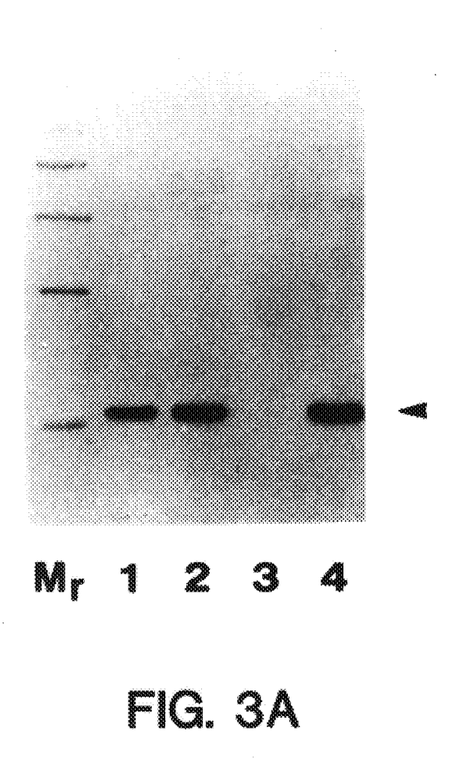
FIGS. 3A and 3B are Western immunoblot showing an analysis of HPV-18 E7 protein and cellular p53 protein in the HPV-18 transfected human prostate epithelial (HPE) clones. The appropriate cell extracts were analyzed using rabbit antisera against either the HPV-18 E7 protein (FIG. 3A) or the cellular p53 protein (FIG. 3B). The molecular weight markers ($M_r$) used were 97.4, 69, 46, 30 and 14.3 kilodaltons. The arrowheads show the approximately 15-kD E7 protein (FIG. 3A) and the 53-kD p53 protein (FIG. 3B). Lanes 1: HPV-18 transfected HPE clone A-2. Lanes 2: HPV-18 transfected HPE clone C-1. Lanes 3: SV40 ori-transfected HPE clone. Lanes 4: HeLa cells.
Figure 3B:
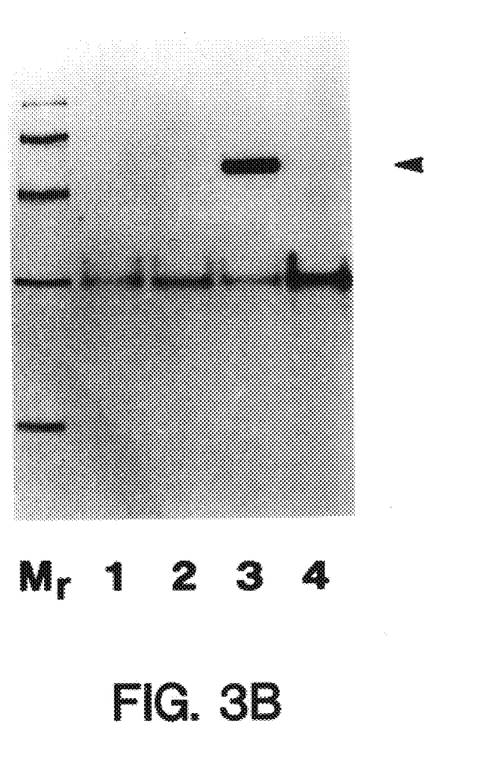

As evidence for the acquisition of the morphological change being the consequence of expression of HPV-18 functions, the presence of the HPV-18 E7 gene product was determined by Western immunoblot analysis the presence of the HPV-18 E7 gene product using a rabbit antibody (Maloy, W. L., et al., Proceedings of the National Academy of Science USA 81:1216–1220 (1984)). Identification of an approximately 15-kD component in both clones A-2 and C-1, that is also present in HeLa cells but not in an SV40 ori-transfected human prostatic epithelial clone, is consistent with transformation requiring at least the expression of the E7 protein. This is seen in FIG. 3A. Interestingly, while the tumor suppressor protein p53 is detected in abundance in the SV40 ori-transfected clone, presumably because of its stabilization by binding to the SV40 T-antigen, it is not detectable in either of the two HPV-18 transfected clones. This is seen in FIG. 3B. This latter observation is consistent with E7 destabilizing p53, a process which has been proposed to result in the loss of tumor suppressor activity.

Evidence for the human origin of the two lines was obtained by isoenzyme analysis and cell membrane species-specific immunofluorescence. Moreover, both cell lines showed human karyotype with a Y chromosome. When clone C-1 was analyzed at passage 11 and clone A-2 at passage 15, both were aneuploid and had five and nine marker chromosomes, respectively.

Immunocytochemical analysis showed that both cell lines expressed cytokeratins 8 and 18, which are specific epithelial cell markers. Prostate-specific antigen was strongly present in parental cells, in early passages of both clones as well as in later passages of cell lines treated with the androgen 5α-dihydrotestosterone.

When analyzed for biological properties, it was observed that neither cell line grew in soft agar or produced tumors in 129J nude mice even when $10^7$ cells were injected as shown in Table 1. Thus, HPV-18 infection was associated with the continued proliferative capacity of adult human prostatic epithelial cells in culture without the concomitant acquisition of a neoplastic phenotype.

In attempts to alter the growth properties of human prostatic epithelial cells, Ki-MuSV was used, since activated Ki-ras oncogene has been detected in human prostate carcinomas (Viola et al., N. Engl. J. Med. 314:133–137 (1986); Carter, B. S. et al Cancer Research 50, 6830–6832 (1990); and Konishi, N., et al., Cancer 69, 2293–2299 (1992), and HPV-18, which has also been detected in human prostate carcinomas (McNicol, N. J., et al., Journal of Urology 145, 850–853 (1991); and Anwar, K., et al., Cancer Research 52, 5991–5996 (1992).

Ki-MuSV was produced in human nonproducer cells by superinfection with the baboon endogenous virus (BaEV) (Rhim, J. S., et al., Science 227:1250–1252 (1985). The cells are neomycin resistant. At passage 12, the HPV-18 immortalized prostatic cell line was transformed by infection with Ki-MuSV. The characteristics of the resulting immortalized HPV-18+Ki-MuSV cell line were determined and compared to parental cells, the HPV-18 immortalized cell line or to Ki-MuSV infected cells. Neither control parental nor Ki-MuSV infected cells could be propagated serially beyond five subcultures.

In contrast, infection of the HPV-18 transfected C-1 line at passage 12 with Ki-MuSV, pseudotyped with baboon endogenous virus (Table 1) to facilitate entry into human cells, resulted in a marked alteration in cell morphology. Two to three weeks after infection, the cells began to pile up in focal areas as shown in FIG. 1B. The absence of any detectable alteration induced by the helper virus alone implied that Ki-MuSV was responsible for inducing the transformed morphology.

Figure 4:
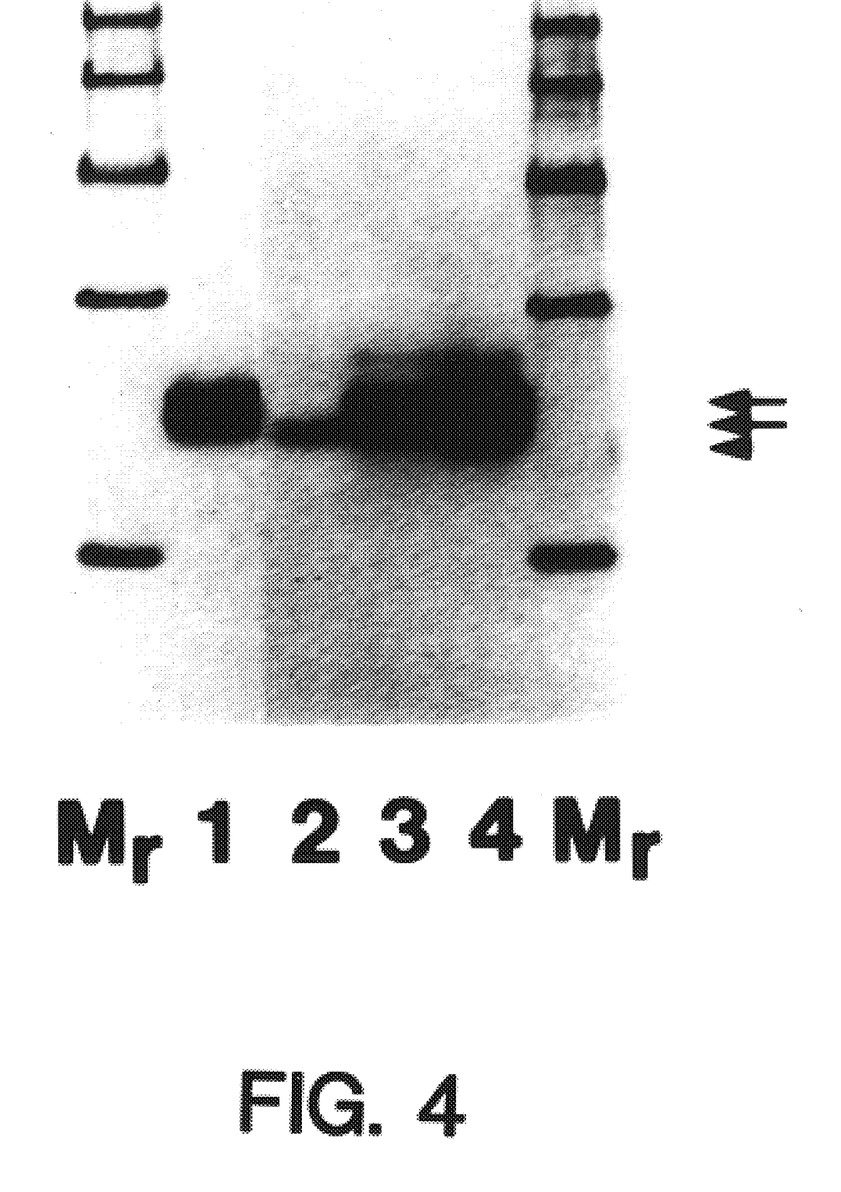

The presence and expression of the Ki-ras oncogene in the transformant was confirmed by Western immunoblot analysis using a pan reactive mouse antibody against the ras p21 protein. Using this analysis, the C-1 clone was found to express a low level of the endogenous p21 protein as indicated on a SDS-polyacrylamide gel by a characteristic doublet (FIG. 4, lane 2) which represents the phosphorylated and non-phosphorylated forms of the gene product (Rhim, J. S., et al., Science, 232:385–388 (1986)). In addition to the endogenous p21, the Ki-MuSV transformed C-1 line also expressed a high level of the activated Ki-ras gene product which is distinguishable by its slower migration on SDS-polyacrylamide gels (FIG. 4, lane 3). The expression of the activated ras gene in the transformant is further supported by the presence of the transfected v-Ki-ras gene, as shown by Southern blot hybridization analysis (data not shown). HPV-18 DNA analysis indicated that its copy number in the Ki-MuSV transformed C-1 cells has remained unchanged (data not shown).

EXAMPLE 3

When adult 129J nude mice were inoculated subcutaneously with $10^7$ Ki-MuSV-transformed C-1 cells, tumors developed within 3-weeks at the site of inoculation as shown in Table 1. Microscopic examination of sections of these tumors revealed poorly differentiated carcinomas consistent with neoplastic transformation of the human prostate epithelial cells as shown in FIG. 1C. The tumor consists of large, poorly-differentiated epithelial cells with hyperchromatic, irregularly-shaped nuclei. The presence of a high mitotic index is consistent with rapid cell division. Structures resembling epithelial pearls are evident suggesting squamous cell differentiation. Small nondescript cells displaying little cytoplasm are admixed amongst the tumor cells.

Tumors were re-established in culture and confirmed as human epithelial cells by isoenzyme and cytokeratin analyses. Their identity with the cells of origin was determined by karyological analysis. The cultured tumor cells continued to express the activated Ki-ras gene product, as confirmed by Western immunoblot analysis (FIG. 4, lane 4). Prostate tumor cell lines were then reinjected into athymic nude mice, resulting in rapid tumor formation at a frequency of 100% (5/5). In contrast, subcutaneous inoculation of $10^7$ parental C-1 cells produced no tumors during the observation period of six months.

The present invention represents the first malignant transformation of adult human prostate epithelial cells in culture and supports previous epidemiological studies that have implicated the Ki-ras oncogene and HPV infection in prostatic carcinogenesis. It has been demonstrated that expression of the v-Ki-ras gene in an HPV-18 immortalized adult human prostatic epithelial cell line facilitates malignant transformation. Two or more alterations in cellular growth properties seem to be required. The process was indicated by the acquisition of an unlimited growth potential as a result of HPV-18 gene expression. In addition to acquiring a continuous proliferation capacity, the HPV-18 transfected human prostatic epithelial cells showed an abnormal karyotype at the earliest measurable time. Nonetheless, they lacked the ability to induce progressively growing tumors in nude mice. Thus, the alterations induced by HPV-18 DNA transfection are necessary but by themselves are insufficient to induce progression to the neoplastic state. Various virus can induce a cell to become tumorigenic, e.g. oncogenic retrovirus.

Superinfection of early passage HPV-18 immortalized adult human prostate epithelial cells with Ki-MuSV, a virus with an activated Ki-ras oncogene (v-Ki-ras), resulted in further changes in their growth properties. Expression of the activated ras-21 protein, morphological alteration, increase in genetic instability and ability to induce squamous cell carcinomas in athymic nude mice appeared to be concomitantly-acquired properties associated with the addition of the v-Ki-ras oncogene. The significance of the combined action of HPV-18 and the v-Ki-ras oncogene in the induction of malignant transformation of human prostatic epithelial cells is emphasized by the finding that the v-Ki-ras gene alone cannot induce neoplastic transformation unless the cells have been immortalized by HPV-18. Thus, the v-Ki-ras oncogene has the ability to complement with HPV to induce full transformation.

The results show that successive changes are required to induce malignant transformation of human prostatic epithelial cells of adult origin, the natural target of prostate carcinogenesis. The multi-step in vitro model is invaluable for defining the molecular events underlying the development of human prostate cancer.

The following points demonstrate the significance of the novel malignant and non-malignant cell lines:

1. Specimens of normal human prostate are very difficult to obtain because of the availability and consent concerns.
2. The non-malignant cell lines were immortalized by using the human papillomavirus (HPV) DNA. The importance of this rests in the fact that certain HPV's (HPV-16, HPV-18) are sexually transmitted and are associated with the development of cancer of the cervix. About 95% of women with cervical cancer are found to be positive of HPV. It therefore stands to reason that in some genital cancers in men, these sexually transmitted HPV's may also be involved. It was for this reason that HPV DNA was used.
3. HPV-18 DNA has been detected in samples of human prostate cancers.
4. No other HPV-immortalized, human prostatic cell lines have been developed.
5. Assuming that HPV's are involved in human prostate cancer, then the cell models will also be extremely useful for studying the interactions between HPV and prostatic cells during the cancer development process.
6. Both types of cell lines (malignant and non-malignant) are useful. The non-malignant cell lines do not form tumors and retain many properties of normal cells. Therefore, they can be used in place of normal cells for research.
7. The use of human cell models is much more appropriate than using rat or mouse cells, data from which then have to be extrapolated to the human condition.
8. The use of cell models for research is preferred as much as possible in order to avoid unnecessary use of whole animals.

The applications for the cell lines are in the areas of cancer research; research studying aging; cancer prevention; role of diet and nutrition in cancer; cell physiology: studies on the mechanisms of secretion; cell biology; biochemistry; studies on cell differentiation; developmental biology; and all biomedical sciences.

Thus the cell lines can be used in:
1. Cancer Prevention: as models for the discovery and testing of agents which may have the ability to prevent prostate cancer and benign prostate hyperplasia (BPH).
2. Cancer detection and diagnosis: as models for discovering new markers for early detection of prostate cancer and BPH.
3. Basic Research: The cell models can be used for a large variety of studies, for example:
    (a) identification of agents which cause prostate cancer and BPH.
    (b) the origin and the process of cancer development in the human prostate.
    (c) mechanisms of tumor progression and its control.
    (d) multistep process of carcinogenesis, especially as we have the normal, immortalized and malignant cells derived from the same prostate.
    (e) for the identification of specific genetic defects which lead to the development of prostate cancer.
    (f) for studies on why prostate cancer does not respond well to chemotherapy.
    (g) mechanisms of drug resistance in prostate cancer and how to circumvent resistance.
    (h) basic understanding of prostate physiology and its role in reproduction.
4. Models for Risk Assessment of Reproductive toxicity:
    Reproductive toxicity may result in infertility in men, spontaneous abortions in their female partners and birth defects in their offspring. The cells can be used as
    (a) a model for identification of reproductive toxins which may be secreted into the seminal fluid and thus damage sperm, resulting in birth defects.
    (b) a model for detection of exposure to environmental and industrial reproductive toxins.
    (c) a model for detection of reproductive toxicity in men exposed to chemicals in chemical warfare.
    (d) a model for infertility and for birth defects in the offspring of men exposed to toxic chemicals in the industry and in chemical warfare.
5. Models for Alternatives to Animal Testing:
    There is presently a great deal of concern about the use of animals for testing products for human use. With the upsurge of interest in the Animal Rights Movement, considerable emphasis is being placed on the development of cell culture models as alternative to using animals for testing. The drug and the cosmetic industry and manufacturers of household and industrial chemicals are interested in using cell culture models, especially those derived from human cells, to test for human toxicity of their products.
6. Cancer Treatment:
    (a) as cell systems for the discovery of new drugs such as cisplatin and taxol, for the treatment of prostate cancer and BPH.
    (b) as cell models for examining the efficacy of single drugs and combination of drugs and/or radiation for the treatment of prostate tumors.
    (c) as cell systems for identification of anti-invasive agents such as protease inhibitors and other agents which can specifically prevent invasion and thus, can be used to prevent cancer from invading the neighboring tissues.
    (d) as cell models for identification of anti-metastasis agents, which can specifically prevent cancer from metastasizing and spreading to different organs.
7. Identification of potential chemotherapeutic drugs:
    These cells are useful for screening chemicals suitable for the treatment of cancer and related diseases, by growing them in vitro in medium containing the chemical to be tested and then, after a suitable period of exposure, determining whether and to what extent cytotoxicity has occurred, e.g. by trypan blue exclusion assay or related assays (Paterson, Methods Enzymol. 58:141–152 (1979)), or by growth assays such as colony forming efficiency (MacDonald et al., Exp. Cell. Res. 50:471–473 (1968)), all of which are standard techniques well known in the art.

Similarly, potential chemotherapeutic drugs may be screened in vivo in suitable animal models. The tumorigenic human prostate epithelial cell lines are injected subcutaneously into athymic nude mice. Potential chemotherapeutic drugs are injected at various time intervals and doses. Animals are examined weekly for the presence of tumors for a period of four or more months.
8. Studies of metabolism of carcinogens and other: xenobiotics
    Carcinogens and other xenobiotics may be added to the growth medium of cultures of these cells and then the appearance of metabolic products of these compounds may be monitored by techniques such as thin layer chromatography or high performance liquid chromatography and the like. The interactions of the compounds and/or their metabolites with DNA can then be examined.
9. Studies of DNA mutagenesis: Substances known or suspected to be mutagens may be added to the growth medium of cell cultures, especially the immortalized RWPE-1 cells, and then mutations may be assayed, e.g., by detection of the appearance of drug resistant mutant cell colonies (Thompson, Methods Enzymol., 48:308–322 (1979)). Similarly, cell-mediated DNA mutagenesis, by cocultivating the cells with cell types known or suspected to be capable of activating mutagenic compounds (Hsu et al., Proc. Natl. Acad. Sci. USA 75:2003–2007 (1978)).

10. Studies of chromosome damaging agents: Substances known or suspected to cause chromosomal damage may be added to the culture medium of these cell lines, and then the extent of chromosomal damage may be measured by techniques such as measurement of the frequency of sister chromatid exchange (Latt et al. In: S. Wolff (ed.), Sister Chromatid Exchanges, New York: Plenum Press, pp. 17–40, (1982)).

11. Studies of malignant transformation by chemical, physical and viral agents, and transferred genes including other oncogenes in addition to, or in place of the Ki-ras oncogene and high molecular weight genomic DNA from tumors, using standard assays such as tumor formation in athymic nude mice.

12. Studies of cellular responses to growth factors, cytokines tumor promotors/enhancers, or hormones and production of growth factors, cytokines, tumor promotors/enhancers, or hormones: Identification and purification of novel growth factors, cytokines, tumor promotors/enhancers, or hormones important for growth and differentiation of human prostate epithelial cells. These cells are particularly useful for such an application since they grow in serum-free media. Therefore, responses to growth factors, cytokines, tumor promotors/enhancers, or hormones can be studied in precisely defined growth media and any factors produced by the cells may be identified and purified without the complication of the presence of serum. In addition to the isolation and characterization of growth factors, cytokines, tumor promotors/enhancers or hormones produced endogenously by the cells of the present invention, exogenous sources of growth factors, cytokines, tumor promotor/enhancers or hormones are added and the effect on growth and differential determined. Moreover, various chemical agents are added in the presence of the endogenous or exogenous growth factors, cytokines, tumor promotors/enhancers or hormones and the effect on cell growth and differential determined. The chemical agents may be a chemotherapeutic agent, a carcinogenic agent or any chemical agent known or suspected of having an effect on cell growth and/or cell differentiation.

13. Use of recombinant DNA expression vectors to produce proteins of interest. For example, the gene encoding a protein of therapeutic value may be recombined with controlling DNA segments (i.e. containing a promoter with or without an enhancer sequence), transferred into the cell (e.g. by polybrene transfection) and then the protein produced may be harvested from the culture supernatant or a cellular extract by routine procedures well known in the art.

14. Characterization of cell surface antigens or receptors: The cells are incubated with an antibody against the cell surface antigen or receptors of interest, and then reacted with a second antibody which is conjugated to a fluorescent dye. The cells are then evaluated using a fluorescence activated cell sorter to determine whether they are fluorescent and therefore possess the cell surface antigen or receptors. Novel surface antigens or receptors are purified and isolated from the cells of the present invention by immunoaffinity chromatography using antibody specific for the antigen or receptor, using the specific ligand to the receptor or using other chromatographic techniques known in the art.

15. Cell-cell hybrid studies for identification of tumor suppressor activity (Stanbridge et al., Science 215:252–259 (1982)). To determine whether immortalized non-malignant cell lines contain tumor suppressor genes, they are fused to malignant tumor cells. The presence of tumor suppressor genes in hybrid cells is indicated by loss of malignant properties, i.e., loss of in vitro characteristics of cancer cells, such as loss of density dependent inhibition of growth, growth in agar, stimulation of growth by autocrine secretion of growth factors and loss of ability to form tumors in athymic nude mice and chick chorioallantoic membrane.

16. Identification of novel genes, including transforming genes in naturally occurring cancers, growth factor genes, oncogenes, tumor suppressor genes, using standard molecular biological techniques (Davis et al., Methods in Molecular Biology, New York: Elsevier, 167–189 (1986)) and techniques such as cDNA substraction cloning and the like.

17. Studies of cellular Biochemistry, including changes in cellular physiology such as changes in intracellular pH and calcium levels and the like, as correlated with cell growth and action of exogenous agents. To study intracellular pH and calcium levels, cells in suitable culture vessels are exposed to fluorescence emissions are detected with a fluorescence spectrophotometer (Grynkiewicz et al, J. Biol. Chem. 260:3440–3450 (1985)).

18. Studies of intercellular communication e.g., by dye scrape loading assays. To determine whether the cells growing in vitro have the ability to communicate via gap junctions, the cultures may be scraped, e.g., with a scalpel, in the presence of a fluorescent dye in the growth medium. Cells at the edge of the wound are mechanically disrupted and therefore take up dye. Intercellular communication is ascertained by determining whether cells distant from the wound also contain dye.

The kit for screening carcinogenic or antineoplastic agents and for any other usage as described herein supra, is easily assembled, comprising the cell line(s) of the present invention. Other components routinely found in such kits may also be included with instructions for performing the test.

The fibroblast cells are associated with prostatic epithelial cells and thus the interactions of the cells can be studied using the cells of the present invention.

An application by some of the inventors herein is co-pending describing prostatic cells immortalized with Adenovirus 12 and Simian virus 40.

It is intended that the foregoing description be only illustrative of the present invention and that the present invention be limited only by the hereinafter appended claims.

We claim:

1. A method for testing an agent for the ability to Prevent invasiveness of a malignant cell line comprising culturing a malignant human prostatic epithelial or fibroblast cell line containing DNA of human papillomavirus 18, which immortalizes the cell line, and transformed with an activated Ras oncogene, which causes the cell line to become malignant in nude mice, with a potential anti-invasive agent wherein inhibition of invasion by the cell line indicates that the agent prevents invasiveness.

2. The method of claim 1 wherein the cell line is deposited as ATCC CRL-11610.

3. A method for testing the ability of a chemical agent to prevent invasiveness by a malignant human prostatic epithelial or fibroblast cell line comprising culturing the malignant cell line containing DNA of human papillomavirus 18, which immortalizes the cell line, and transformed with an activated Ras oncogene, which causes the cell line to become malignant and form tumors when injected into nude mice, in an invasion assay with the chemical agent and determining whether the agent prevents the invasive ability of the cell line.

* * * * *